United States Patent [19]

Cuervo et al.

[11] Patent Number: 4,962,277
[45] Date of Patent: Oct. 9, 1990

[54] DELETION ANALOGUES OF MAGAININ PEPTIDES

[75] Inventors: Julio H. Cuervo, Cardiff; Richard A. Houghten, Solana Beach, both of Calif.

[73] Assignee: Scripps Clinic and Research Foundation, La Jolla, Calif.

[21] Appl. No.: 281,981

[22] Filed: Dec. 9, 1988

[51] Int. Cl.[5] .......................... A61K 37/02; C07K 7/08
[52] U.S. Cl. ......................................... 514/14; 514/13; 530/324; 530/325; 530/326; 530/327
[58] Field of Search ............... 530/324, 325, 326, 327; 514/12, 13, 14

[56] References Cited

U.S. PATENT DOCUMENTS 4,810,777 3/1989 Zasloff ............................... 530/326

Primary Examiner—Lester L. Lee
Attorney, Agent, or Firm—Dressler, Goldsmith, Shore, Sutker & Milnamow, Ltd.

[57] ABSTRACT

A compound comprising a deletion analogue of an amide or carboxy-terminating Magainin I of the following structural formula using the single letter amino acid code:

G I G K F L H S A G K F G K A F V G E I M K S
1 2 3 4 5 6 7 8 9 10 11 12 13 14 15 16 17 18 19 20 21 22 23 and wherein at least one of amino acid residues 15 through 23 is omitted;

or a deletion analogue of an amide or carboxy-terminated Magainin II of the following structural formula using the single letter amino acid code:

G I G K F L H S A K K F G K A F V G E I M N S
1 2 3 4 5 6 7 8 9 10 11 12 13 14 15 16 17 18 19 20 21 22 23 and wherein at least one of amino acid residues 15 through 23 is omitted. These compounds can be effectively used as pharmaceutical compositions.

45 Claims, 3 Drawing Sheets

DELETION ANALOGUES OF MAGAININ PEPTIDES

This invention relates to a class of biologically active peptides known as magainins. More particularly, this application relates to analogues of magainin peptides wherein at least one amino acid residue in the peptide has been omitted from the peptide chain, said analogues are commonly referred to as "deletion analogues."

In accordance with an aspect of the present invention, there is provided a compound comprising a peptide deletion analogue of an amide or carboxy terminated Magainin I, wherein Magainin I is represented by the following structural formula using the single letter amino acid code and the numbers below each amino acid residue refer to the position of the residue in the peptide:

```
G I G K F L H S A G K F G K A F V G E I M K S
1 2 3 4 5 6 7 8 9 10 11 12 13 14 15 16 17 18 19 20 21 22 23
``` and at least one of amino acid residues 15 through 23 is omitted. In a preferred embodiment, at least one of amino acid residues 15, 16, 18, 19, 21, 22 and 23 is omitted. In one embodiment, at least amino acid residue 18 is omitted whereas in another embodiment. at least amino acid residue 19 is omitted, and in yet another embodiment at least amino acid residue 21 is omitted. In preferred embodiments, only one of amino acid residues 18, 19, and 21, respectively, is omitted. In other preferred embodiments, amino acid residues 21, 22, and 23 are omitted, amino acid residues 19 through 23 are omitted, amino acid residues 18 through 23 are omitted and amino acid residues 17 through 23 are omitted. The compound can be a deletion analogue of amide - or carboxy-terminated Magainin I.

The deletion analogues are referred to hereinafter in short-hand form by use of a minus sign (−), the single letter code for the amino acid residue, and a superscript numeral that indicates the position of the residue in the sequence. A reference to Magainin I or II is also made.

In accordance with another aspect of the present invention, there is provided a compound comprising a peptide that is deletion analogue of an amide - or carboxy-terminated Magainin II, wherein Magainin II is represented by the following structural formula using the single letter amino acid code and the numbers below each amino acid residue refer to the position of the residue in the peptide:

```
G I G K F L H S A K K F G K A F V G E I M N S
1 2 3 4 5 6 7 8 9 10 11 12 13 14 15 16 17 18 19 20 21 22 23
``` and at least one of amino acids 15 through 22 is omitted. In a preferred embodiment, at least one of amino acids 15, 18, 19, 20, 21, and 22 is omitted. In one embodiment, at least amino acid 18 is omitted. In another embodiment, at least amino acid 19 is omitted. Another embodiment omits at least amino acid 21, and yet other embodiment omits at least amino acid 22. In preferred embodiments, only one of amino acids 18, 19, 21, and 22, respectively, is omitted. The compound can be a deletion analogue of amide terminated Magainin II.

It has been found that the deletion analogues of Magainin I and Magainin II, as described above, are effective against Gram-positive and Gram-negative bacteria while having insignificant hemolytic action against human red blood cells.

The use of these compounds which comprise a deletion analogue of Magainin I or Magainin II peptide, in accordance with the present invention, is effective as an antibiotic, and can be employed to inhibit, prevent or destroy the growth or proliferation of microbes, such as bacteria, fungi viruses or the like. Similarly, such compounds can be employed as an anti-viral composition to inhibit, prevent or destroy the growth or proliferation of viruses.

Such compounds can also be employed as a spermicide to inhibit, prevent or destroy the motility of sperm.

Such compounds can also be employed as anti-tumor agents to inhibit the growth of or destroy tumors.

The compounds have a broad range of potent antibiotic activity against a plurality of microorganisms, including Gram-positive and Gram-negative bacteria, fungi, protozoa and the like. Such compounds can be employed for treating or controlling microbial infection caused by organisms which are sensitive to such compounds.

The compounds can also be used as preservatives or sterilants for materials susceptible to microbial contamination.

Although the present invention is not to be limited by any theoretical reasoning, preliminary NMR studies indicate that the conformation of Magainin 11 is solvent dependent changing from a random coil in water to an α-helix in a more hydrophobic solvent such as trifluoroethanol. These results suggest that magainins have the potential to be induced into an α-helix configuration when in contact with the lipid membrane of the various microbial organisms.

In general, the deletion analogue of the Magainin I or Magainin II peptide is administered in a dosage of from about 1mg to about 500 mg per kilogram of body weight, when administered systemically. When administered topically, the peptide is used in a concentration of from about 0.5% to about 5%.

The compounds comprising the deletion analogues of Magainin I or Magainin II, in accordance with the present invention, can be employed for treating a wide variety of hosts. In accordance with a preferred embodiment, a host can be an animal, and such animal can be a human or non-human animal.

The compounds comprising the deletion analgoues of Magainin I or Magainin II can be employed in a wide variety of pharmaceutical compositions in combination with a non-toxic pharmaceutical carrier or vehicle such as a filler, non-toxic buffer, or physiological saline solution. Such pharmaceutical compositions can be used topically or systemically and can be in any suitable form such as a liquid, solid, semi-solid, injectable solutions, tablet, ointment, lotion, paste, capsule or the like. The compounds comprising the deletion analogues of Magainin I or Magainin II can also be used in combination with adjuvants, protease inhibitors, or compatible drugs where such a combination is seen to be desirable or advantageous in controlling infection caused by harmful microorganisms including protozoa, viruses, and the like.

The compounds comprising the deletion analogues of Magainin I or Magainin II of the present invention can be administered to a host: in particular an animal, in an effective antibiotic and/or anti-tumor and/or anti-viral and/or anti-microbial and/or a spermicidal amount.

Magainin I and Magainin II, as well as the deletion analogues of the Magainin I and Magainin II peptides of the present invention, (both amide- and carboxy-terminated Magainin I and Magainin II forms) can be synthesized by any convenient method of peptide synthesis as are well-known to skilled workers. Solid phase synthesis methods are particularly preferred.

The peptides described herein were prepared by the method of simultaneous multiple peptide synthesis (SMPS). This method is described in detail in Houghten, R. A., "General Method for the Rapid Solid-Phase Synthesis of Large Numbers of Peptides; Specificity of Antigen-Antibody Interaction at the Level of Individual Amino Acids," *Proc. Natl. Acad. Sci. U.S.A.*, Vol. 82, pgs. 5131–5135 (1985), and in Houghten, R. A., et al. "Simultaneous Multiple Peptide Synthesis; The Rapid Preparation of Large Numbers of Discrete Peptides for Biological, Immunological, and Methodological Studies," *Peptide Chemistry*, pgs. 295–298 (1987). By this method, a complete series of omission, or deletion, analogues, can be prepared.

For purposes of the following examples, a series of deletion analogues is comprised of a series of 23 peptides wherein amino acid residue 1 is omitted from the first peptide, amino acid 2 is omitted from the second peptide, etc., up to the deletion analogue wherein amino acid 23 is omitted from the twenty-third peptide. A series of deletion analogues can thus be prepared for both Magainin I and Magainin II.

For purposes of comparison, complete Magainin I and Magainin II peptides which are amide-terminated or carboxy-terminated, can also be prepared by the SMPS method. It is also contemplated within the scope of the present invention that deletion analogues which have more than one amino acid residue omitted from the Magainin I or Magainin II structure can also be prepared. Such peptides are described in Example 5.

The invention will now be described with respect to the drawings, wherein.

Figure 2A:
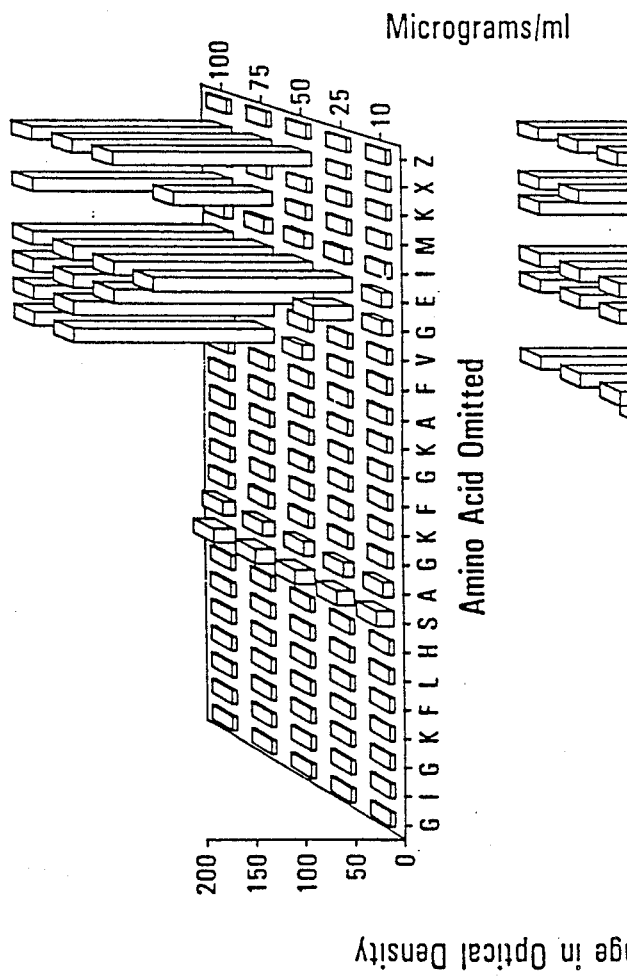
FIG. 2a is a graph of 1/(change in optical density) vs. micrograms/ml of peptide for samples containing Magainin I or analogue and *S.epidermis*.
Figure 2B:
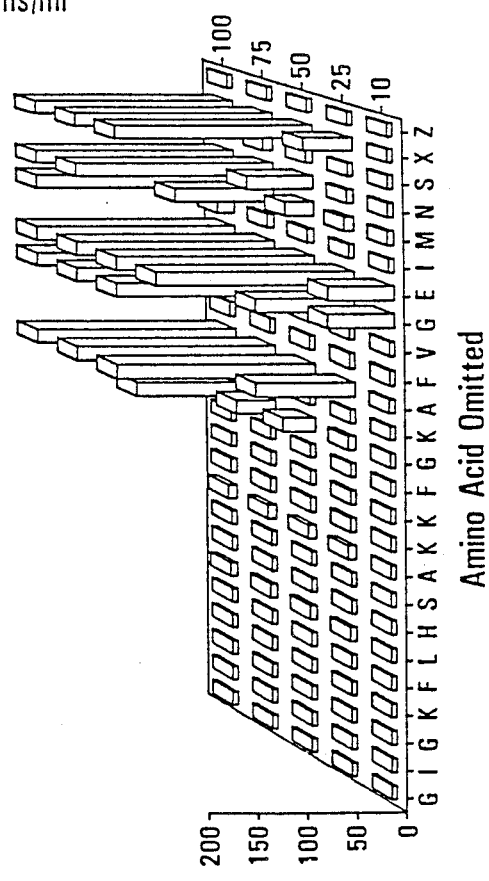
Figure 3:
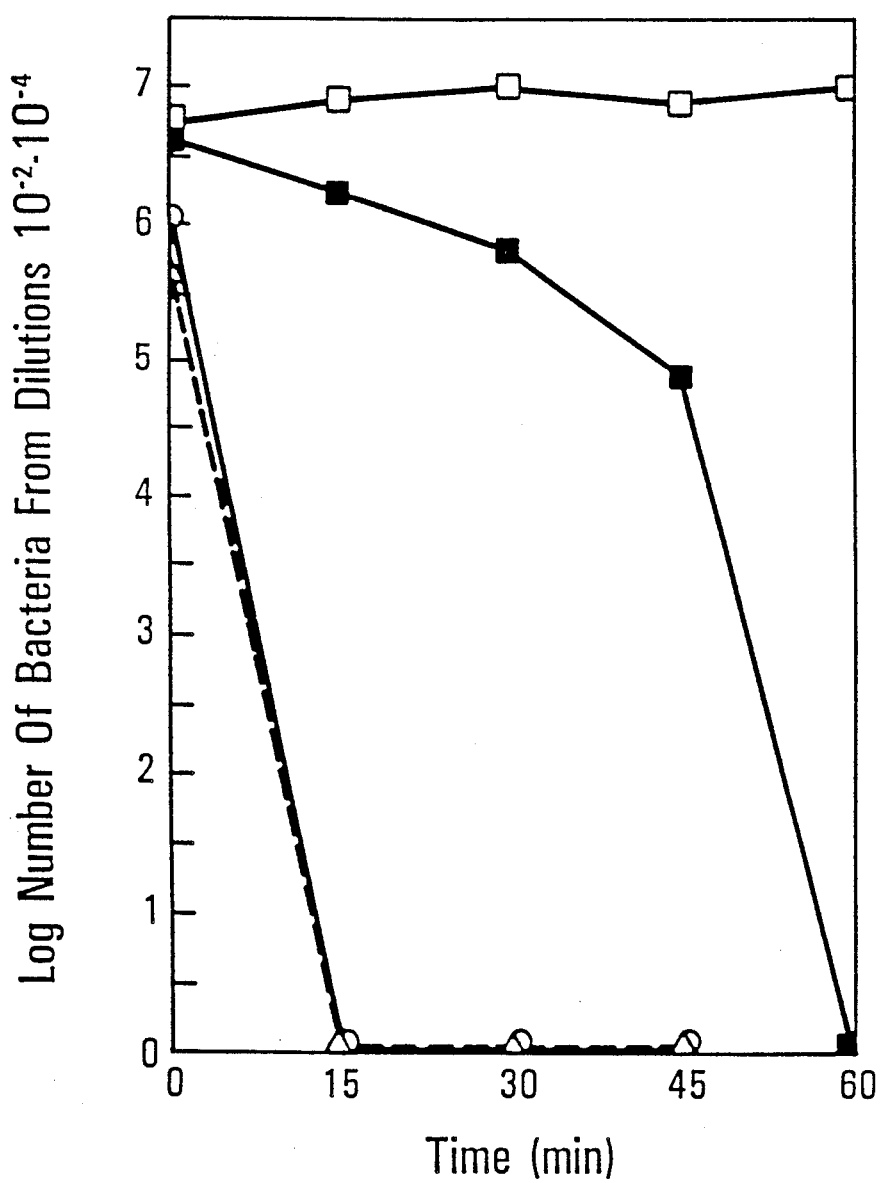

FIG. 2b is a graph of 1/(change in optical density) vs. micrograms/ml of peptide for samples containing Magainin II or analogue and *S.epidermis*: and FIG. 3 is a graph of the log (number of bacteria from $10^{31 2}$, $10^{-3}$, and $10^{-4}$ dilutions of $1.0 \times 10^6$ CFU/ml *E.coli*) vs. time that *E.coli* organisms were incubated with the $-G^{18}$ deletion analogue of Magainin II (), the $-E^{19}$ deletion analogue Magainin II (—), amide-terminated Magainin II (□), or a control (□).

The invention will now be described with respect to the following examples, however, the scope of the present invention is not intended to be limited thereby.

Example 1 - Peptide Synthesis

Peptide synthesis of Magainin I, Magainin II and the deletion analogues, was accomplished by using the strategy of simultaneous multiple peptide synthesis. All solvents and reagents were of analytical grade and were used without further purification. Standard N-t-Boc-protected amino acids were employed in the synthesis. The side chain functionalities used were benzyl (Ser. Glu), 2-Cl-Z (Lys)(Z=benzyloxycarbonyl), $N^{im}$- DNP His), and sulfoxide (Met). Peptide synthesis was performed beginning with 100 mg of either Boc-amino acids-Pam resin to produce C-terminal carboxyl peptide (PAM purchased from applied Biosystems, substitution 0.56 meq/gm is an amino acyl -4- [oxymethyl]phenylacetic acid derivative of amino polystyrene) or methylbenzhydrylamine resin (substitution-0.65 meq/gm) per resin packet to produce C-terminal amide peptide.

After synthesis, completely protected peptide resins were treated three times with 0.5M thiophenol in DMF to remove the $N^{im}$- dinitrophenyl group from Histidine. The final Boc-group was removed with TFA to avoid t-butylation of methionyl residues during final HF treatment. Cleavage was performed using the Low-High HF procedure. Tam. et al. J. Am. Chem. Soc. Vol. 105, P. 6442 (1983). For peptides synthesized on Pam resin the low-HF was carried out without removing the resin from the packet, using a multiple vessel HF apparatus for 2 hrs, at 0° C. For peptides prepared using MBHA resin, the low HF procedure was performed in a common reaction vessel for 2 hrs. at 0° C. For Pam resin peptides, the low-HF mixture was evacuated from the 24 individual reaction vessels by a water aspirator followed by a mechanical pump. Once the dimethylsulfide (derived from the low step) and the HF were removed the peptides were subjected to high HF (10% anisole) for 1½ hrs. at −5° C. 0° C. HF was evaporated by a strong flow of nitrogen. The low-HF reaction vessel containing the bags with MBHA resin was emptied of the low-HF mixture by pouring off the liquid into a waste container. The bags were washed immediately with cold ether followed by alternating washes of $CH_2Cl_2$, DMF, $CH_2Cl_2$, IPA. $CH_2Cl_2$. The packets were then dried and put into individual tubes of the 24 vessel HF apparatus with 0.7 ml of anisole as scavenger. The high-HF was performed by condensing dry hydrogen fluoride at −70° C. The reaction took place at −10° C. for 1 h. and −5° C. - 0° C. for the last 30 min. HF was evaporated using a strong flow of nitrogen. Finally, residual carbonium ion scavengers were removed by washing with dry ether.

The crude peptides were subsequently extracted with 10% acetic acid and subjected to RP-HPLC on an analytical reversed phase column (Vidac ODS 25 cm×4.6 mm), using a Beckman-Altek model 421 HPLC system and two model 110A pumps. The solvent system was composed of buffer A, 0.05% TFA/H20, and buffer B, 0.05% TFA/$CH_3CN$ with a flow rate of 1.0 ml/min. The peptides were detected at 215 nm using a Hitachi 100–20 spectrophotometer.

Purification of the peptides was accomplished by reverse - phase HPLC on a Vidac C18 (22 mm×25 cm), 10 μm packing column with an eluting gradient composed of $CH_3CN$ and 0.05% TFA. Amino acid analysis was carried out on a Beckman 6300 analyzer following hydrolysis of the peptides in constant (boiling) 6 N HCl at 110° C. for 24 hr., and such analysis was within ±10% of theory.

Example 2 - Antimicrobial Assays

Antimicrobial assays were carried out in 96 -well tissue culture plates. Each well was incubated with a given microorganism suspended in LB medium (*Escherichia coli*, and *Staphylococcus epidermis* or YTB medium (*Candida albicans*). Upon the addition of the peptides or their deletion analogues, (dissolved in 1×PBS, pH 7.0)

each well contained a final cell density of $1.0 \times 10^6$ colony forming units (CFU)/ml. The final peptide concentrations used were 100 μg/ml., 75.0 μg/ml, 50.0 μg/ml, 25 μg/ml, and 10 μg/ml Concentrations of up to 500 μg/ml, however, were employed against *C. albicans.*

Addition of peptides to the wells was defined as time zero. At six hours, the plates were placed in a Titertek Multiskan apparatus and the O.D.$_{620}$ determined. The plates as well as the initial innoculum were incubated at 37° C.

Five wells per plate contained media alone. while five others contained medium plus cells. These controls were used to eliminate the possibility of media contamination while providing a measure of uninhibited growth of the microorganisms. The measurements of 1/(change in optical in density) for the wells containing either the peptides or their deletion analogues in the above-mentioned varying concentrations with the colony forming units of *E. coli* or *S. epidermis* are shown in FIGS. 1 and not tested.) FIG. 2b is a graph pertaining to Magainin II (indicated by X) and its deletion analogues. In both graphs, Z is a control of medium plus cells. The measurements of 1/(change in optical density) as measured for the Magainin I and Magainin II peptides and their deletion analogues can be correlated to a measurement of their effectivness against *E. coli* and *S. epidermis.*

The degree of peptide activity was determined by comparing the deletion analogs with uninhibited growth of the control cells over a six-hour period. The effective growth inhibition of each of the peptides and their deletion analogues is listed below in Table 1. As listed in Table 1, M1C is Magainin I, C-terminal carboxyl carboxy-terminated), whereas M2A, is Magainin II, C-terminal amide (amide-terminated). The letter and number code after each M1C or M2A peptide indicates the amino acid residue deleted from the particular deletion analogue of Magainin I carboxY-terminated) or Magainin II (amide-terminated).

TABLE 1

| | Effective Growth Inhibition* (Concentration in μg/ml) | | | | | |
|---|---|---|---|---|---|---|
| | E. coli | | S. epidermis | | C. albicans | |
| Peptide** | % Inhibit/ Conc. M1C | % Inhibit/ Conc. M2A | % Inhibit/ Conc. M1C | % Inhibit/ Conc. M2A | % Inhibit/ Conc. M1C | % Inhibit/ Conc. M2A |
| M1C/M2A | 100 at 50 | 100 at 25 | 100 at 50 | 93 at 25 | 80 at 500 | ND |
| M1C-S$^{23}$/M2A-S$^{23}$ | ND | 100 at 25 | ND | 0 at 100 | 0 at 100 | ND |
| M1C-K$^{22}$/M2A-N$^{22}$ | 100 at 75 | 100 at 25 | 0 at 100 | 100 at 75 | 0 at 500 | ND |
| M1C-M$^{21}$/M2A-M$^{21}$ | 95 at 50 | 95 at 25 | 94 at 75 | 90 at 75 | 0 at 500 | ND |
| M1C-I$^{20}$/M2A-I$^{20}$ | 100 at 75 | 84 at 25 | 0 at 100 | 0 at 100 | 0 at 500 | ND |
| M1C-E$^{19}$/M2A-E$^{19}$ | 100 at 25 | 92 at 10 | 100 at 25 | 89 at 10 | 0 at 500 | ND |
| M1C-G$^{18}$/M2A-G$^{18}$ | 100 at 25 | 94 at 10 | 88 at 25 | 89 at 10 | 0 at 500 | ND |
| M1C-V$^{17}$/M2A-V$^{17}$ | 92 at 50 | 87 at 50 | 100 at 75 | 0 at 100 | 87 at 500 | ND |
| M1C-F$^{16}$/M2A-F$^{16}$ | 100 at 50 | 92 at 100 | 100 at 75 | 0 at 100 | 0 at 500 | ND |
| M1C-A$^{15}$/M2A-A$^{15}$ | 100 at 50 | 95 at 10 | 0 at 100 | 90 at 25 | 80 at 400 | ND |
| M1C-K$^{14}$/M2A-K$^{14}$ | 100 at 100 | 87 at 50 | 0 at 100 | 0 at 100 | 0 at 500 | ND |
| M1C-G$^{13}$/M2A-G$^{13}$ | 90 at 100 | 89 at 25 | 0 at 100 | 80 at 50 | 0 at 500 | ND |
| M1C-F$^{12}$/M2A-F$^{12}$ | 0 at 100 | 0 at 100 | 0 at 100 | 0 at 100 | 0 at 500 | ND |
| M1C-K$^{11}$/M2A-K$^{11}$ | 0 at 100 | 0 at 100 | 0 at 100 | 0 at 100 | 0 at 500 | ND |
| M1C-G$^{10}$/M2A-K$^{10}$ | 0 at 100 | 0 at 100 | 0 at 100 | 0 at 100 | 0 at 500 | ND |
| M1C-A$^9$/M2A-A$^9$ | 0 at 100 | 82 at 75 | 0 at 100 | 0 at 100 | 0 at 500 | ND |
| M1C-S$^8$/M2A-S$^8$ | 0 at 100 | 90 at 75 | 0 at 100 | 0 at 100 | 0 at 500 | ND |
| M1C-H$^7$/M2A-H$^7$ | 0 at 100 | 90 at 100 | 0 at 100 | 0 at 100 | 0 at 500 | ND |
| M1C-L$^6$/M2A-L$^6$ | 0 at 100 | 0 at 100 | 0 at 100 | 0 at 100 | 0 at 500 | ND |
| M1C-F$^5$/M2A-F$^5$ | 0 at 100 | 0 at 100 | 0 at 100 | 0 at 100 | 0 at 500 | ND |
| M1C-K$^4$/M2A-K$^4$ | 0 at 100 | 80 at 100 | 0 at 100 | 0 at 100 | 0 at 500 | ND |
| M1C-G$^3$/M2A-G$^3$ | 0 at 100 | 93 at 100 | 0 at 100 | 0 at 100 | 0 at 500 | ND |
| M1C-I$^2$/M2A-I$^2$ | 0 at 100 | 0 at 100 | 0 at 100 | 0 at 100 | 0 at 500 | ND |
| M1C-G$^1$/M2A-G$^1$ | 0 at 100 | 0 at 100 | 0 at 100 | 0 at 100 | 0 at 500 | ND |
| M1-Amide/M2-Amide | 100 at 25 | 100 at 25 | 90 at 25 | 93 at 25 | 0 at 500 | ND |
| M1-Carboxy/M2-Carboxy | 100 at 50 | 100 at 50 | 100 at 50 | 100 at 50 | 80 at 50 | ND |

*% Inhibition $= \left(1 - \dfrac{\Delta \text{Abs}(T_6 - T_1) \text{ with omission analog}}{\Delta \text{Abs}(T_6 - T_1) \text{ of no peptide control}}\right) \times 100$ % Reported if greater than 80%. In the above Table, if % Inhibition is less than 100%, % Inhibition at next higher concentration equals 100%.

**M1C = Magainin 1, C terminal-carboxyl
M2A = Magainin 2, C terminal-amide

Figure 1A:
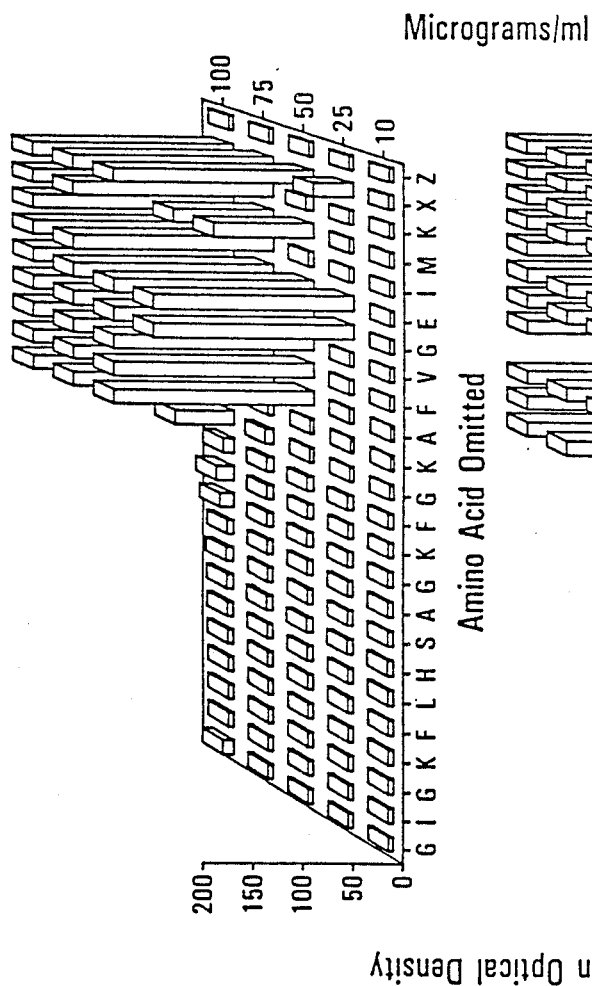
FIG. 1a is a graph of 1/(change in optical density), vs. micrograms/ml of peptide for samples containing Magainin I or analogue and *E.coli*.
Figure 1B:
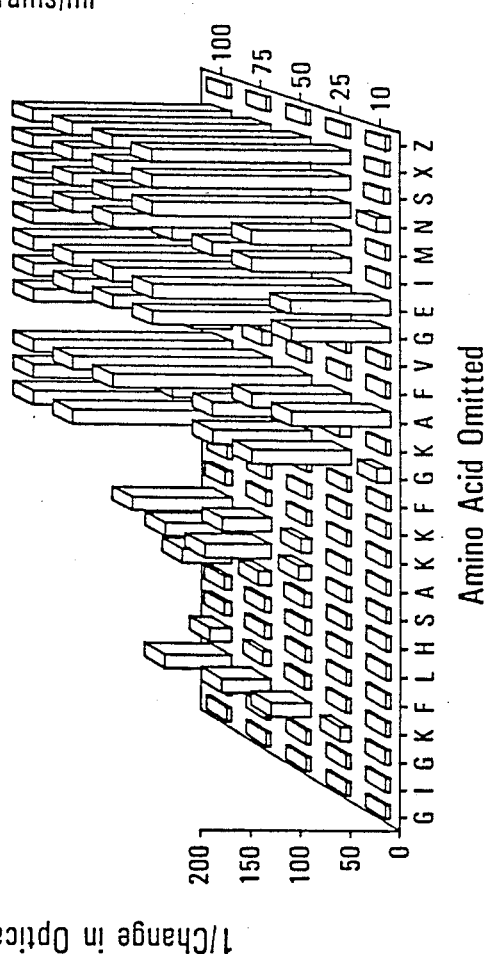
FIG. 1b is a graph of 1/(change in optical density) vs. micrograms/ml of peptide for samples containing Magainin II or analogue and *E. coli*.

2. FIG. 1 is a graph of the measurements of 1/(change in optical density) for wells containing Magainin I or Magainin II peptides or their deletion analogues and *E. coli.* FIG. 1a is a graph pertaining to Magainin I (indicated by X) and its deletion analogues. (The deletion analogue wherein amino acid 23 omitted was not tested). FIG. 1b is a graph pertaining to Magainin II (indicated by X) and its deletion analogues. In both graphs, Z is a control of medium plus cells.

FIG. 2 is a graph of the measurements of 1/(change in optical density) for wells containing Magainin I or Magainin II peptides or their deletion analogues and *S. epidermis.* FIG. 2a is a graph pertaining to Magainin I (indicated by X) and its deletion analogues. (The deletion analogue wherein amino acid 23 was deleted was It has also been found that the antimicrobial effectiveness of crude Magainin I and Magainin II peptides and crude deletion analogue preparations was identical, within experimental error, to that of purified Magainin I and Magainin II peptides and their deletion analogues.

As indicated in Table 1 above, as well as in FIGS. 1 and 2, analogues having a peptide deletion in the N-terminal region (amino acids 1-14), had a decrease in the peptide's activity against *E. coli* and *S. epidermis.* The omission of glycine (amino acid 18) or glutamic acid (amino acid 19) from either Magainin I or Magainin II resulted in the most active deletion analogues for both Magainin I and Magainin II when compared to their relative inhibitory concentration. With *C. albicans,* none of the deletion analogues were active at 100 μg/ml, but when tested at 400μg/ml, the deletion analogue of Magainin I wherein alanine (amino acid 15) had been deleted had low but significant activity.

Upon comparison to the full sequence of both Magainin I and Magainin II, it was found that peptides having a C-terminal amide were more active than those with a C-terminal carboxy. For Magainin I amide, at a peptide concentration of 25 μg/ml, 100% inhibition of the growth of *E. coli* was found. However, only 70% growth inhibition was detected for the corresponding carboxy form at 25 μg/ml. For the amide and carboxyl forms of Magainin II, the differences in antimicrobial potency with *E. coli* were more significant. As shown in Table 1, the C-terminal carboxy form of Magainin II showed 100% inhibition at 50 μg/ml, whereas Magainin II amide showed 100% inhibition at 25 μg/ml.

Example 3 - Kinetics of Microbial Killing

Dissolved peptide preparations of amide-terminated Magainin II, amide-terminated Magainin II with glycine (amino acid 18) deleted, and amide-terminated Magainin II with glutamic acid (amino acid 19) deleted were added to test tubes containing *E. coli* ($1.0 \times 10^6$ CFU/ml) to a final peptide concentration of 25 μg/ml. At the time points of 15, 30, 45, and 60 minutes after the addition, indicated in FIG. 3, 10.0 μl were removed from each tube and sequentially diluted by a factor of ten four times in LB medium. The number of bacteria at each time point was determined by plating 10.0 μl of the $10^{-2}$, $10^{-3}$, and $10^{-4}$ dilutions. The log of the number of bacteria from these dilutions at each time point was determined, and was plotted on the graph in FIG. 3. Two controls, one with medium alone and one with no peptides were both incubated along with the tubes containing cells and peptides. The tubes as well as the agar plates used were incubated at 37° C.

As shown in FIG. 3, the growth of *E. coli* When incubated with the $-G^{18}$ or $-E^{19}$ deletion analogue of Magainin II was rapidly halted. In each case, all *E. coli* cells were killed within 15 minutes of addition of the peptide preparation. The full sequence of amide-terminated Magainin II was much slower in achieving complete killing of *E. coli* than the $-G^{18}$ and deletion analogues. Thus, the and $-E^{19}$ deletion analogues of amide-terminated Magainin II achieved a significantly higher rate of cell lysis in *E. coli*.

Example 4 - Human Red Blood Cell Hemolysis

The hemolytic activity of the Magainins and their omission analogues was examined with human red blood cells. Ten μl of blood were suspended in isotonic PBS buffer (pH 7) followed by the addition of the peptide to reach a final volume of 1 ml. The suspension was gently mixed and then incubated for 30 min. at 37° C. The samples were centrifuged at 1000 g for 5 min. The supernatant was separated from the pellet and the optical density was measured at 414 nm. 100% Hemolysis was determined by disrupting the human erythrocytes in pure $H_2O$. The results are indicated in Table 2 below.

TABLE 2

| Peptide* | % Hemolysis of Human Red Blood Cells Concentration | | | | | | | | | |
|---|---|---|---|---|---|---|---|---|---|---|
| | φμg/ml | | 75 μg/ml | | 50 μg/ml | | 25 μg/ml | | 10 μgm/ml | |
| M1C/M2A | 2 | 4 | 2 | 2 | 1 | 2 | 0 | 0 | 0 | 0 |
| M1C-S$^{23}$/M2A-S$^{23}$ | ND | 1 | ND | 1 | ND | 1 | ND | 0 | ND | 0 |
| M1C-K$^{22}$/M2A-N$^{22}$ | 0 | 2 | 0 | 0 | 0 | 0 | 0 | 0 | 0 | 0 |
| M1C-M$^{21}$/M2A-M$^{21}$ | 1 | 0 | 0 | 0 | 0 | 0 | 0 | 0 | 0 | 0 |
| M1C-I$^{20}$/M2A-I$^{20}$ | 1 | 0 | 0 | 0 | 0 | 0 | 0 | 0 | 0 | 0 |
| M1C-E$^{19}$/M2A-E$^{19}$ | 1 | 0 | 0 | 0 | 0 | 0 | 0 | 0 | 0 | 0 |
| M1C-G$^{18}$/M2A-G$^{18}$ | 1 | 4 | 0 | 4 | 0 | 4 | 0 | 3 | 0 | 0 |
| M1C-V$^{17}$/M2A-V$^{17}$ | 1 | 0 | 1 | 0 | 1 | 0 | 0 | 0 | 0 | 0 |
| M1C-F$^{16}$/M2A-F$^{16}$ | 1 | 1 | 0 | 0 | 0 | 0 | 0 | 0 | 0 | 0 |
| M1C-A$^{15}$/M2A-A$^{15}$ | 1 | 4 | 1 | 3 | 1 | 3 | 0 | 3 | 0 | 0 |
| M1C-K$^{14}$/M2A-K$^{14}$ | 0 | 1 | 0 | 1 | 0 | 0 | 0 | 0 | 0 | 0 |
| M1C-G$^{13}$/M2A-G$^{13}$ | 0 | 3 | 0 | 2 | 0 | 2 | 0 | 1 | 0 | 0 |
| M1C-F$^{12}$/M2A-F$^{12}$ | 0 | 1 | 0 | 1 | 0 | 1 | 0 | 0 | 0 | 0 |
| M1C-K$^{11}$/M2A-K$^{11}$ | 1 | 1 | 1 | 0 | 0 | 0 | 0 | 0 | 0 | 0 |
| M1C-G$^{10}$/M2A-K$^{10}$ | 1 | 1 | 1 | 0 | 0 | 0 | 0 | 0 | 0 | 0 |
| M1C-A$^9$/M2A-A$^9$ | 0 | 0 | 0 | 0 | 0 | 0 | 0 | 0 | 0 | 0 |
| M1C-S$^8$/M2A-S$^8$ | 0 | 0 | 0 | 0 | 0 | 0 | 0 | 0 | 0 | 0 |
| M1C-H$^7$/M2A-H$^7$ | 0 | 0 | 0 | 0 | 0 | 0 | 0 | 0 | 0 | 0 |
| M1C-L$^6$/M2A-L$^6$ | 0 | 1 | 0 | 0 | 0 | 0 | 0 | 0 | 0 | 0 |
| M1C-F$^5$/M2A-F$^5$ | 0 | 1 | 0 | 1 | 0 | 0 | 0 | 0 | 0 | 0 |
| M1C-K$^4$/M2A-K$^4$ | 0 | 2 | 0 | 1 | 0 | 0 | 0 | 0 | 0 | 0 |
| M1C-G$^3$/M2A-G$^3$ | 0 | 0 | 0 | 0 | 0 | 0 | 0 | 0 | 0 | 0 |
| M1C-I$^2$/M2A-I$^2$ | ND | 0 | ND | 0 | ND | 0 | ND | 0 | ND | 0 |
| M1C-G$^1$/M2A-G$^1$ | ND | 0 | ND | 0 | ND | 0 | ND | 0 | ND | 0 |

*M1C = Magainin I, C-terminal carboxyl
M2A = Magainin II, C-terminal amide

As shown in Table 2 above, amide-terminated Magainin II showed 2% hemolysis while carboxy-terminated Magainin I showed 1% hemolysis at 50 μg/ml. No lysis of human erythrocytes was detected at 25 μg/ml for either Magainin I or Magainin II. The $-G^{18}$ and $-E^{19}$ deletion analogues of both Magainin I and Magainin II showed no hemolytic activity at 10 μg/ml. which is the minimal inhibtory concentration shown in the antimicrobial assays of Example 2.

Also as shown in Table 2, there was decreased hemolytic activity in the deletion analogues of Magainin I wherein any one of amino acids 15 through 22 was deleted, at concentrations of 100 and 75 μg/ml. At 50 μg/ml. there was decreased hemolytic activity in the deletion analogues of Magainin I wherein any one of amino acids 16, 18, 19, 20, 21, or 22 was deleted. There was also decreased hemolytic activity for the deletion analogues of Magainin II wherein any one of amino acids 16, 17, 19, 20, 21, or 22 was deleted, at concentrations of 100, 75, and 50 μg/ml.

Thus, it is found that these deletion analogues of Magainin I and Magainin II cause less hemolysis of human red blood cells than Magainin I and Magainin II. Thus, it is desirable to use certain deletion analogues which, although not showing increased anti-microbial activity over Magainin I or Magainin II, show a decrease in hemolysis of red blood cells.

Example 5 - Effective Growth Inhibition of *E. coli* for Amide-Terminated Deletion Analogues of Maoainin I Having Multiple Peotide Deletions Deletion analogues of amide-terminated Maginin I were prepared by the simultaneous multiple peptide synthesis method as hereinabove described. The peptides prepared for in use in this example have amino acid residue 23 deleted, have amino acid residues 22 and 23 deleted, have amino acid residues 21, 22 and 23, deleted and so on, up to a peptide which has amino acid residues 17 to 23 deleted.

Each peptide was then incubated in a well of a tissue culture plate with *E. coli* suspended in LB medium. Upon the addition of the deletion analogues (dissolved in 1×PBS, pH 7.0). each well contained a final cell density of $1.0 \times 10^6$ colony forming units (CFU)/ml. Addition of the peptide to the wells was defined as time zero. The final peptide concentrations used were 100 µg/ml, 75.0 µg/ml, 50.0 µg/ml, and 25 µg/ml. The peptides were incubated with the *E. coli* organisms for a period of 6 hours at 37° C. At six hours, the plates were placed in a Titertek Multiskan apparatus and the $O.D._{620}$ was determined.

The degree of peptide activity was determined by comparing the deletion analogues with the original sequences as to the relative ability to inhibit growth of *E. coli* over a six-hour period. The effective growth inhibition of each of the peptide is listed below in Table 3. For purposes of explanation of Table 3 below, the "B" at the end of each peptide indicates the amide-terminal of the Magainin I deletion analogue.

TABLE 3

| Peptide (Amide-terminated Magainin I Deletion Analogue) | Amino Acid Residues Deleted | Minimal Inhibitory Concentration vs. *E. coli* |
|---|---|---|
| GIGKFLHSAGKFGKAFVGEIMKB | 23 | 100% at 25 mg/ml |
| GIGKFLHSAGKFGKAFVGEIMB | 22 and 23 | 100% at 75 mg/ml |
| GIGKFLHSAGKFGKAFVGEIB | 21 to 23 | 100% at 50 mg/ml |
| GIGKFLHSAGKFGKAFVGEB | 20 to 23 | 100% at 100 mg/ml |
| GIGKFLHSAGKFGKAFVGB | 19 to 23 | 100% at 25 mg/ml |
| GIGKFLHSAGKFGKAFVB | 18 to 23 | 100% at 50 mg/ml |
| GIGKFLHSAGKFGKAFB | 17 to 23 | 100% at 50 mg/ml |

As hereinabove stated, it has been postulated that both Magainin I and Magainin II can adopt an α-helix conformation. Several approaches have been used to determine the relationship between the structural properties of the peptides and their biological activity. Although the present invention is not to be limited to any theoretical reasoning, one approach that provides a more general foundation for investigating the structure-activity relationship results from omission of single amino acid residues in the peptide chain. Since the omission of amino acid residues along the peptide chain contracts the peptide backbone, thus leading to new spatial orientation of the side chains, such analogs when induced into an α-helix should assume a new presenting configuration. Thus, key omissions which constrain the backbone in such a way as to favor more stable amphipathic conformations can be important factors in the design of biologically active peptides. There are many physical methods that can be used to determine the structure and dynamics of peptides, but undoubtedly, the most crucial test for Which these molecules can be subjected is their biological activity Comparison of deletion analogues with Magainin I and Magainin II indicates that the N-terminus of Magainin I and Magainin II is important for their antimicrobial activity. Any omission in residues 1–14 was found to have a negative effect on the antibiotic action, as shown in Example 2 and Table 1. If the Magainin peptides adopt an amphipathic conformation upon contact with the lipid membrane of the microorganisms, there appears to be a necessity for these peptides to keep their natural backbone and/or presenting conformational arrangement.

However, the antimicrobial potency exhibited by the series of omission analogs of Magainin I and Magainin II amide was slightly different. This seems to be in agreement with previous reports which cite the greater activity of Magainin II. Zasloff. M., *Proc. Nat. Acad. Sci.*, Vol. 84, pgs. 5449–5453 (1987). As evidenced by the data shown herein omission of serine (amino acid residue 8), alanine (amino acid residue 9), glycine (amino acid residue 13) or to a lesser extent, glycine (amino acid residue 3), in Magainin I and II showed different activities against *E. coli* as indicated in Table 1. With *S. epidermis*, no substantial difference in antimicrobial activity was found between the omission analogs at the N-terminal (residues 1–14) of either Magainin I and Magainin II.

The disruption of the helical character of the N-terminal Magainin I analogs by the omission of key amino acid residues can be expected to decrease their ability to interact with microbial membranes. In general, N-terminal omission analogs in Magainin II can be tolerated without the same loss of activity seen in the N-terminal omission of Magainin I analogues. Since the only difference in the N-terminal region is the substitution of a lysine for glycine in Magainin II, it is believed that lysine, a strongly α-helix inducing residue, may be a key amino acid involved in the stabilization of Magainin II.

The C-terminal region has a greater tendency to maintain activity after amino acid residue omission for both types of analogues. However, C-terminal analogs show some species selectivity as opposed to the N-terminal analogs which lack activity in *E. coli* and *S. epidermis*. Thus, *E. coli* was more sensitive than *S. epidermis* to exposure to the omission analogs at the C-terminal region of both Magainin I and Magainin II.

The omission of the hydrophobic residues phenylalanine (amino acid residue 16) or valine (amino acid residue 17) in Magainin II seems to be the most important modification which decreases the antimicrobial activity in both *E. coli* and *S. epidermis*. When the isoleucine 20 omission analog of synthetic Magainin I was tested no activity was found against *S. epidermis* while 75 μg/ml of the isoleucine 20 omission analog was needed to inhibit the growth of *E. coli* completely. In both Magainin I and Magainin II there was a need to preserve those hydrophobic residues at these positions. The lower or complete loss of antimicrobial activity upon omission of phenylalanine 16 valine 17, or isoleucine 20 may indicate that the Magainin peptides need the hydrophobic character provided by these amino acids to intereact with the lipopolysaccharide of the bacterial membrane although the scope of the present invention is not intended to be limited to this reasoning. Since the only difference between Magainin I and Magainin II in the carboxy-terminal region is the K (lysine) for the more hydrophobic N (asparagine) in position 22, the former conclusion may help to explain why Magainin II showed more activity than Magainin I. Another observation that supports this conclusion is the substantially higher activity of the Magainins having the C-terminal amide.

The high antimicrobial activity of the omission analogues glycine 18 and glutamic acid 19 together with their low hemolysis of red cells in comparison to the full sequences of Magainin I and Magainin II makes these two analogues good candidates for clinical application. The strong antimicrobial potency displayed by the glycine 18 omission analogues in both Magainins can be explained by the omission of glycine which has a low potential for helix formation. On the other hand, the omission of glutamic acid 19, a negatively charged amino acid residue, from a peptide which is predominantly positive becomes an issue. Perhaps the removal of this negatively charged amino acid residue facilitates the interaction with the negatively charged lipopolysaccharide layer of the bacteria. The increase of activity and the decrease of red blood cell lysis as compared to the initial Magainin sequences highlights this omission analog as being potentially important in clinical applications.

It has also been found that better stability and a better storage period for the peptide is obtained in a deletion analogue from which methionine has been omitted.

Numerous modifications and variations of the present invention are possible in light of the above teachings, and, therefore, within the scope of the accompanying claims, the invention may be practiced other than as particularly described.

What is claimed is:

1. A compound comprising:
a deletion analogue of an amide or carboxy terminated Magainin I wherein Magainin I is represented by the following structural formula using the single letter amino acid code and the numbers below each amino acid residue refer to the position of the residue in the peptide:

G I G K F L H S A G K F G K A F V G E I M K S
1 2 3 4 5 6 7 8 9 10 11 12 13 14 15 16 17 18 19 20 21 22 23 and at least one of amino acids 15 through 23 is omitted.

2. The compound of claim 1 wherein at least one of amino acids 15, 16, 18, 19, 21, 22 and 23 is omitted.

3. The compound of claim 2 wherein at least amino acid 18 is omitted.

4. The compound of claim 2 wherein at least amino acid 19 is omitted.

5. The compound of claim 2 wherein at least amino acid 21 is omitted.

6. The compound of claim 2 wherein at least amino acid 22 is omitted.

7. The compound of claim 2 wherein at least amino acid 23 is omitted.

8. The compound of claim 3 wherein only amino acid 18 is omitted.

9. The compound of claim 4 wherein only amino acid 19 is omitted.

10. The compound of claim 5 wherein only amino acid 21 is omitted.

11. The compound of claim 1 wherein the compound is a deletion analogue of amide terminated Magainin I.

12. The compound of claim 1 wherein the compound is a deletion analogue of carboxy terminated Magainin I.

13. The compound of claim 2 wherein amino acids 21, 22 and 23 are omitted.

14. The compound of claim 1 wherein amino acids 19, 20, 21, 22 and 23 are omitted.

15. The compound of claim 1 wherein amino acids 18, 19, 20, 21, 22 and 23 are omitted.

16. The compound of claim 1 wherein amino acids 17, 18, 19, 20, 21, 22 and 23 are omitted.

17. A compound comprising:
a deletion analogue of an amide or carboxy terminated Magainin II wherein Magainin II is represented by the following structural formula using the single letter amino acid code and the numbers below each amino acid residue refer to the position of the residue in the peptide:

G I G K F L H S A K K F G K A F V G E I M N S
1 2 3 4 5 6 7 8 9 10 11 12 13 14 15 16 17 18 19 20 21 22 23 and at least one of amino acids 15 through 22 is omitted.

18. The compound of claim 17 wherein at least one of amino acids 15, 18, 19, 20, 21, and 22 is omitted.

19. The compound of claim 18 wherein at least amino acid 18 is omitted.

20. The compound of claim 18 wherein at least amino acid 19 is omitted.

21. The compound of claim 18 wherein at least amino acid 21 is omitted.

22. The compound of claim 18 wherein at least amino acid 22 is omitted.

23. The compound of claim 19 wherein only amino acid 18 is omitted.

24. The compound of claim 20 wherein only amino acid 19 is omitted.

25. The compound of claim 21 wherein only amino acid 21 is omitted.

26. The compound of claim 22 wherein only amino acid 22 is omitted.

27. The compound of claim 17 wherein the compound is a deletion analogue of amide terminated Magainin II.

28. A process for inhibiting growth or proliferation of microbes comprising:
administering to microbes whose growth or proliferation is to be inhibited a pharmaceutical composition containing the compound of claim 1 in an effective growth or proliferation inhibiting amount.

29. A process for inhibiting growth or proliferation of microbes comprising:

administering to microbes whose growth or proliferation is to be inhibited a pharamceutical composition containing the compound of claim 4 in an effective growth or proliferation inhibiting amount.

30. A process for inhibiting growth or proliferation of microbes comprising:
administering to microbes whose growth or proliferation is to be inhibited a pharamceutical composition containing the compound of claim 16 in an effective growth or proliferation inhibiting amount.

31. A process for inhibiting growth or proliferation of microbes comprising:
administering to microbes whose growth or proliferation is to be inhibited a pharamceutical composition containing the compound of claim 17 in an effective growth or proliferation inhibiting amount.

32. A process for inhibiting growth or proliferation of microbes comprising:
administering to microbes whose growth or proliferation is to be inhibited a pharamceutical composition containing the compound of claim 20 in an effective growth or proliferation inhibiting amount.

33. An inhibiting growth or proliferation of microbes pharamceutical composition comprising the compound in an effective amount of claim 1 and a pharmaceutical carrier.

34. An inhibiting growth or proliferation of microbes pharmaceutical composition comprising the compound in an effective amount of claim 4 and a pharmaceutical carrier.

35. An inhibiting growth or proliferation of microbes pharmaceutical composition comprising the compound in an effective amount of claim 17 and a pharmaceutical carrier.

36. An inhibiting growth or proliferation of microbes pharmaceutical composition comprising the compound in an effective amount of claim 20 and a pharameutical carrier.

37. An inhibiting growth or proliferation of microbes pharmaceutical composition comprising the compound in an effective amount of claim 14 and a pharameutical carrier.

38. An inhibiting growth or proliferation of microbes pharmaceutical composition comprising the compound in an effective amount of claim 16 and a pharameutical carrier.

39. An inhibiting growth or proliferation of microbes pharmaceutical composition comprising the compound in an effective amount of claim 27 and a pharameutical carrier.

40. An inhibiting growth or proliferation of microbes pharmaceutical composition comprising the compound in an effective amount of claim 2 and a pharmaceutical carrier.

41. An inhibiting growth or proliferation of microbes pharmaceutical composition comprising the compound in an effective amount of claim 18 and a pharmaceutical carrier.

42. An inhibiting growth or proliferation of microbes pharmaceutical composition comprising the compound in an effective amount of claim 11 and a pharmaceutical carrier.

43. An inhibiting growth or proliferation of microbes pharmaceutical composition comprising the compound in an effective amount of claim 12 and a pharmaceutical carrier.

44. The compound of claim 18 where only amino acid 15 is omitted.

45. An inhibiting growth or proliferation of microbes pharmaceutical composition comprising the compound in an effective amount of claim 44 and a pharmaceutical carrier.

* * * * *

UNITED STATES PATENT AND TRADEMARK OFFICE
CERTIFICATE OF CORRECTION

PATENT NO. : 4,962,277
DATED : October 9, 1990
INVENTOR(S) : Cuervo et al.

It is certified that error appears in the above-identified patent and that said Letters Patent is hereby corrected as shown below:

Column 1, after the title and before the first paragraph, insert the following paragraph:

--This invention was made with government support under Contract No. DIR 8713707 awarded by the National Science Foundation. The government has certain rights in the invention.--

Signed and Sealed this

Eighth Day of February, 1994

*Attest:*

BRUCE LEHMAN

*Attesting Officer*    Commissioner of Patents and Trademarks